(12) United States Patent
Hunter

(10) Patent No.: US 12,311,004 B2
(45) Date of Patent: May 27, 2025

(54) OPHTHALMIC FORMULATIONS AND METHODS OF USE

(71) Applicant: VISION SOLUTIONS, LLC, Tucson, AZ (US)

(72) Inventor: Brian A. Hunter, Tucson, AZ (US)

(73) Assignee: VISION SOLUTIONS, LLC, Tucson, AZ (US)

( * ) Notice: Subject to any disclaimer, the term of this patent is extended or adjusted under 35 U.S.C. 154(b) by 0 days.

(21) Appl. No.: 18/897,657

(22) Filed: Sep. 26, 2024

(65) Prior Publication Data

US 2025/0099524 A1 Mar. 27, 2025

Related U.S. Application Data

(60) Provisional application No. 63/585,825, filed on Sep. 27, 2023.

(51) Int. Cl.

| | |
|---|---|
| *A61K 36/236* | (2006.01) |
| *A61K 9/00* | (2006.01) |
| *A61K 31/198* | (2006.01) |
| *A61K 45/06* | (2006.01) |
| *A61K 47/02* | (2006.01) |
| *A61P 27/02* | (2006.01) |

(52) U.S. Cl.
CPC .......... *A61K 36/236* (2013.01); *A61K 9/0048* (2013.01); *A61K 31/198* (2013.01); *A61K 45/06* (2013.01); *A61K 47/02* (2013.01); *A61P 27/02* (2018.01)

(58) Field of Classification Search
None
See application file for complete search history.

(56) References Cited

U.S. PATENT DOCUMENTS

2002/0197313 A1* 12/2002 Richardson .............. A61K 9/06 514/474

FOREIGN PATENT DOCUMENTS

| CA | 2615200 | A1 | 7/2009 |
| CN | 104435857 | A | 3/2015 |
| CN | 104622800 | A | 5/2015 |
| CN | 031692 | B2 * | 10/2019 |
| CN | 111110737 | A | 5/2020 |
| JP | 110302191 | * | 6/1982 |

OTHER PUBLICATIONS

Puerarin, Science Direct, Biomedicine and Pharmacotherapy, 2020, and MCE data sheet, accessed online Nov. 18, 2024, (Year: 2024).*
Stiles et al. "Effect of oral administration of L-lysine on conjunctivitis caused by feline herpesvirus in cats." American Journal of Veterinary Research 63.1 (2002): 99-103.
Nasisse et al. "Effects of valacyclovir in cats infected with feline herpesvirus 1." American journal of veterinary research 58.10 (1997): 1141-1144.
Spertus et al. "Effects of orally administered raltegravir in cats with experimentally induced ocular and respiratory feline herpesvirus-1 infection." American Journal of Veterinary Research 80.5 (2019): 490-497.
Bol, Sebastiaan, and Evelien M. Bunnik. "Lysine supplementation is not effective for the prevention or treatment of feline herpesvirus 1 infection in cats: a systematic review." BMC Veterinary Research 11 (2015): 1-15.
Thiry et al. "Feline herpesvirus infection. ABCD guidelines on prevention and management." Journal of Feline Medicine & Surgery 11.7 (2009): 547-555.
Lucyshyn, Danica R., and Lynne S. Sandmeyer. "Diagnostic Ophthalmology." The Canadian Veterinary Journal 62.7 (2021): 762.
Wagner, Denae C., Philip H. Kass, and Kate F. Hurley. "Cage size, movement in and out of housing during daily care, and other environmental and population health risk factors for feline upper respiratory disease in nine North American animal shelters." PLoS One 13.1 (2018): e0190140.
Contreras et al. "Effect of a pheromone on stress-associated reactivation of feline herpesvirus-1 in experimentally inoculated kittens." Journal of veterinary internal medicine 32.1 (2018): 406-417.
Pennington, Matthew R., Eric C. Ledbetter, and Gerlinde R. Van de Walle. "New paradigms for the study of ocular alphaherpesvirus infections: insights into the use of non-traditional host model systems." Viruses 9.11 (2017): 349.
Paßlack, Nadine, Marcus G. Doherr, and Jürgen Zentek. "Effects of free amino acids on cytokine secretion and proliferative activity of feline T cells in an in vitro study using the cell line MYA-1." Cytotechnology 68 (2016): 1949-1961.
WIPO, "International Search Report and Written Opinion" issued in connection with WIPO Patent Application PCT/US2024/048668, dated Nov. 20, 2024, 10 pages.

* cited by examiner

*Primary Examiner* — Melissa S Mercier
(74) *Attorney, Agent, or Firm* — NGUYEN TARBET IP LAW

(57) ABSTRACT

Feline herpesvirus (FHV-1) is a highly contagious virus affecting domestic and wild felines and is the leading cause of corneal disease and conjunctivitis in cats. Thus, provided herein is topical ophthalmic formulation for treating FHV-1, comprising L-lysine and a second therapeutic agent, such as osha root (e.g., ligustilide). The formulation enables direct and concentrated delivery to the ocular surface, which is believed to enhance efficacy in treating herpesvirus infections. This innovative approach improves treatment outcomes by targeting the virus more effectively at the site of infection.

12 Claims, No Drawings

OPHTHALMIC FORMULATIONS AND METHODS OF USE

CROSS-REFERENCE TO RELATED APPLICATIONS

This application is a non-provisional and claims benefit of U.S. Provisional Application No. 63/585,825 filed Sep. 27, 2023, the specification of which is incorporated herein in their entirety by reference.

FIELD OF THE INVENTION

The present invention relates to ophthalmic formulations, more particularly to ophthalmic formulations comprising L-lysine and methods of use, such as but not limited to treating feline herpesvirus (FHV-1) in cats or other ocular infections in humans or other animals.

BACKGROUND OF THE INVENTION

Feline herpesvirus (FHV-1) is a ubiquitous and very contagious viral infection found in domestic and wild felines. FHV infection is the most common cause of corneal disease and conjunctivitis in cats, accounting for over 90% of corneal and conjunctival disease in the species.

Feline herpesvirus (FHV) belongs to the family Herpesviridae, subfamily Alphaherpesvirinae, genus *Varicellovirus*. The genomic double-stranded DNA of FHV is packaged into an icosahedral capsid surrounded by a proteinaceous tegument and a phospholipid envelope, which contains at least ten glycoproteins. FHV is a cytolytic virus with an affinity for epithelial cells, e.g., epithelial cells of the conjunctival mucosa and cornea. In the feline host, FHV replicates in epithelial cells of both the conjunctiva and the upper respiratory tract, as well as in neurons, e.g., trigeminal ganglia. The neuronal infection enables the virus to establish lifelong latency after primary infection.

Latent chronic infection is the typical outcome of an acute infection, and intermittent reactivation gives rise to viral shedding in oronasal and conjunctival secretions. The two main sources of infection are virus shed by acutely infected cats and virus shed by latently infected cats experiencing reactivation.

The virus enters via the nasal, oral, or conjunctival routes. It causes a lytic infection of the nasal epithelium, spreading to the conjunctival sac, pharynx, trachea, bronchi, and bronchioles. Lesions are characterized by multifocal necrosis of epithelium, with neutrophil granulocyte infiltration and inflammation. Viral excretion starts as soon as 24 hours after infection. Some animals may develop chronic lesions in the upper respiratory tract and ocular tissues. Upon infection, the virus spreads along the sensory nerves and reaches neurons, particularly in the trigeminal ganglia, which are the main sites of latency. Almost all cats experiencing primary infection become lifelong latent carriers.

The most common clinical signs of FHV-1 infection include squinting or closing of the eye, red, swollen tissue surrounding the eye and eyelids, ocular discharge that may range from clear to yellow-greenish in color, salivation, anorexia, and upper respiratory symptoms such as sneezing or nasal discharge. These signs often appear suddenly and are especially common after stressful situations such as travel, boarding, surgery, or illness. In most cases, lifelong treatment for FHV-1 is expected.

Currently, 20 million cats in the USA are being treated for FHV-1 with oral supplementation of L-lysine. However, in vitro studies with FHV-1 have shown that low concentrations of L-lysine have no effect on the replication kinetics of the virus, and oral supplementation of L-lysine can lead to a depletion of arginine in cats, which cannot synthesize this amino acid. Lowering arginine levels systemically is highly undesirable, and low arginine levels can result in hyperammonemia, which may be fatal. There is currently no consensus as to whether oral administration of lysine is safe and effective in the treatment of FHV-1. There have been no studies to date that have shown the efficacy of ophthalmic application of high concentrations of L-lysine on FHV-1.

BRIEF SUMMARY OF THE INVENTION

It is an objective of the present invention to provide pharmaceutical compositions, e.g., ophthalmic formulations, e.g., topical ophthalmic formulations for administration to the eye, comprising L-lysine, and optionally a second therapeutic agent such as but not limited to ligustilide, and methods of use. The pharmaceutical compositions of the present disclosure have been found to treat, reduce, ameliorate, and alleviate FHV-1 in subjects. In some embodiments, the second therapeutic agent comprises ligustilide, providing a synergistic effect for treating, ameliorating, and/or alleviating symptoms of FHV-1. Embodiments of the invention are given in the dependent claims. Embodiments of the present invention can be freely combined with each other if they are not mutually exclusive.

For example, the present invention features methods of treating FHV-1 infection in a subject in need thereof by administering to the eye of the subject a formulation comprising a pharmaceutical composition as described herein, e.g., a pharmaceutical composition comprising a therapeutic amount of L-lysine and ligustilide, wherein the formulation is effective for treating, ameliorating, and/or alleviating symptoms of FHV-1 infection. The present invention is not limited to FHV-1 applications and may be used for other appropriate ocular infections or inflammatory conditions, such as those in humans (e.g, HSV-1, HSV-2, etc.) or other animals.

In some embodiments, the present invention features a topical ophthalmic formulation comprising ligustilide (e.g., a first therapeutic agent), e.g. extracted from Osha root. In other embodiments, the present invention features a topical ophthalmic formulation comprising L-lysine (e.g., a first therapeutic agent). The aforementioned formulations may further comprise a second, third, or fourth therapeutic agent or any combination thereof. For example, the topical ophthalmic formulation comprising ligustilide as the first therapeutic agent may further comprise L-lysine as a second therapeutic agent.

In some embodiments, the present invention features a topical ophthalmic formulation comprising ligustilide (e.g., a first therapeutic agent), e.g., extracted from Osha root, and a second therapeutic agent (e.g., a second therapeutic agent comprising L-lysine). In other embodiments, the present invention features a topical ophthalmic formulation comprising L-lysine (e.g., a first therapeutic agent) and a second therapeutic agent (e.g., a second therapeutic agent comprising ligustilide). In some embodiments, the second therapeutic agent is an antihistamine, an anti-inflammatory agent, an immunosuppressive agent, a steroid, an antiviral agent, an antimycotic agent, or an anti-allergic agent. Additionally, in some embodiments, the aforementioned formulations may further comprise a third or fourth therapeutic agent. For example, the third or fourth therapeutic agent may comprise an antihistamine, an anti-inflammatory agent, an immunosuppressive agent, a steroid, an antiviral agent, an antimycotic agent, or an anti-allergic agent.

In some embodiments, ligustilide (e.g., as a first or second therapeutic agent) in ophthalmic formulations may be present at a concentration ranging from about 1% to 10% w/v (e.g., g/100 mL). In certain embodiments, the concentration of ligustilide may be approximately 5% w/v.

In some embodiments, L-lysine (e.g., as a first or second therapeutic agent) in ophthalmic formulations may be present at a concentration ranging from about 1% to 5% w/v (e.g., g/100 mL). In certain embodiments, the concentration of L-lysine may be approximately 3% w/v.

In certain embodiments, the aforementioned topical ophthalmic formulations may be aqueous, including in the form of eye drops. In some embodiments, the topical ophthalmic formulations described herein may additionally include bacteriostatic water, bacteriostatic saline, polyethylene glycol, polyvinyl alcohol, propylene glycol, povidone, glycerin, mineral oil, a demulcent, or a combination thereof. Alternatively, or in addition, these formulations may also contain a buffer suitable for ophthalmic use. In certain embodiments, the formulations may further comprise a pharmaceutical carrier.

In some embodiments, the formulations described herein are effective in preventing or treating feline herpesvirus-1 (FHV-1). In other embodiments, the formulations are effective in alleviating the symptoms of FHV-1.

In some embodiments, the present invention may further feature methods of preventing or treating feline herpesvirus (FHV-1) in a subject in need thereof. The method may comprise administering to the subject a therapeutically effective amount of an ophthalmic formulation as described herein.

One of the unique and inventive technical features of the present invention is the direct ophthalmic delivery of Ligustilide (e.g., extracted from Osha root) and L-Lysine. Without wishing to limit the invention to any theory or mechanism, it is believed that the technical feature of the present invention advantageously provides for direct and concentrated delivery of the composition to the ocular surface, thereby enhancing its efficacy in the treatment of herpesvirus infections (e.g., feline herpesvirus). None of the presently known prior references or works have the unique inventive technical feature of the present invention.

Osha root, otherwise known as bear root or *Ligusticum porteri*, is native to Mexico, America's Southwest, and the Rocky Mountains. Z-ligustilide is one of the active ingredients in Osha root that has been used for its antiviral, anti-inflammatory, anti-fungal properties. However there are numerous other bioactive components to Osha root, as described below.

Moreover, the prior references teach away from the present invention. For example, existing treatments for herpesvirus involving L-lysine are typically administered as oral supplements. However, oral supplementation of lysine can lead to arginine deficiency, which may result in irritability and, in severe cases, death. According to the National Research Council, the required daily dose of oral lysine is 200-250 mg/day. Supplementing with lysine at levels up to 50 g/kg can increase the basal serum level in an average adult cat from approximately 85 nmol/mL to about 314 nmol/mL. Arginine deficiency is likely to occur at a daily intake exceeding 80 g/kg. Consequently, there is a limited capacity to increase oral supplementation for the treatment of corneal and upper respiratory diseases such as FHV-1.

In contrast, the present invention, as discussed above, utilizes ocular delivery of L-lysine. This method significantly reduces the risk of inducing arginine deficiency through an ophthalmic preparation. Systemic absorption of topical eye drops can be quantified as follows: 36% of the drops spill out of the tear film, and 5% are absorbed by the corneal tissue, resulting in maximum systemic absorption of 59%. Assuming a 3% lysine solution, two daily drops would lead to an equivalent systemic absorption of approximately 1.77 mg/day—about 100 times less than the normal serum levels in healthy adult cats. Therefore, the risk of systemic arginine toxicity is effectively eliminated.

Furthermore, the inventive technical features of the present invention contributed to a surprising result. For example, it was unexpectedly discovered that the topical administration of a formulation containing L-lysine in combination with Z-ligustilide within a sterile, PH-balanced eye drop formulation is effective in treating and alleviating the symptoms of FHV-1. Without wishing to limit the present invention to any theory or mechanism, it is believed that the formulations of the present invention offer substantial advantages over existing treatment methods in reducing the spread of FHV-1, alleviating its symptoms, treating the virus, and minimizing the risk of potentially blinding complications associated with FHV-1.

Additionally, the inventive technical features of the present invention have contributed to another surprising result. For instance, L-lysine, being positively charged, interacts with negatively charged proteins and phospholipids through the formation of salt bridges, which are pH-dependent. Ligustilide, a phthalide with an oxygen double-bonded to an aromatic ring, also carries a positive charge at physiological pH. As a result, the likelihood of interaction between two positively charged molecules would be limited. Thus, the present invention was surprisingly able to create a formulation comprising these two positively charged molecules.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DETAILED DESCRIPTION OF THE INVENTION

Disclosed are the various compounds, solvents, solutions, carriers, and/or components to be used to prepare the compositions to be used within the methods disclosed herein. Also disclosed are the various steps, elements, amounts, routes of administration, symptoms, and/or treatments that are used or observed when performing the disclosed methods, as well as the methods themselves. These and other materials, steps, and/or elements are disclosed herein, and it is understood that when combinations, subsets, interactions, groups, etc. of these materials are disclosed, while specific reference of each various individual and collective combination and permutation of these compounds may not be explicitly disclosed, each is specifically contemplated and described herein.

Definitions

Unless otherwise explained, all technical and scientific terms used herein have the same meaning as commonly understood by one of ordinary skill in the art to which a disclosed invention belongs. The singular terms "a," "an,"

and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999, Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

As used herein, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a cat. In one embodiment, the subject is a mammal (e.g., a cat) having a disease, disorder, or condition described herein. In another embodiment, the subject is a mammal (e.g., a human) at risk of developing a disease, disorder, or condition described herein. In certain instances, the term patient refers to a human.

"Ophthalmically-acceptable" means that the formulation, active agent, excipient, or other material is compatible with ocular tissue; that is, it does not cause significant or undue detrimental effects when brought into contact with ocular tissue. In some instances, actives and/or excipients of the formulation may cause some discomfort or stinging in the eye; however, those excipients are still considered ophthalmically acceptable for the purposes of this application.

"Therapeutically effective amount" means an amount of active ingredient(s) sufficient to treat, manage, prevent, inhibit, or reduce the condition in the eye or alleviate symptoms thereof.

"Derivative" means any analogs, salts, esters, amines, amides, acids and/or alcohols derived from an agent that may be used in place of that agent.

As used herein, the terms "ligustilide," "z-ligustilide," and "e-ligustilide" are used interchangeably.

As used herein, "osmolality" refers to a measure of a concentration relative to the mass of the solvent. Without wishing to limit the present invention to any theory or mechanism, is it believed that the osmolarity of a solution can have a significant impact on treated tissue properties (e.g., absorption, diffusion, etc . . . ).

The present invention may feature ophthalmic formulations, e.g., topical formulations that are ophthalmically-acceptable for administration to the eye. In some embodiments, the formulations comprise L-lysine, and in some embodiments, comprise a second therapeutic agent, such as but not limited to ligustilide, which is one of the main bioactive components of Osha root. In other embodiments, the formulation comprises ligustilide and, optionally, a second therapeutic agent, such as L-lysine. The present invention also features methods utilizing the formulations herein, for example, for treating feline herpesvirus (FHV-1).

In some embodiments, the present invention features a topical ophthalmic formulation comprising ligustilide (e.g., a first therapeutic agent), e.g. extracted from Osha root. In other embodiments, the present invention features a topical ophthalmic formulation comprising L-lysine (e.g., a first therapeutic agent).

In some embodiments, the present invention features a topical ophthalmic formulation comprising ligustilide (e.g., a first therapeutic agent), e.g., extracted from Osha root, and a second therapeutic agent (e.g., a second therapeutic agent comprising L-lysine). In other embodiments, the present invention features a topical ophthalmic formulation comprising L-lysine (e.g., a first therapeutic agent) and a second therapeutic agent (e.g., a second therapeutic agent comprising ligustilide).

In some embodiments, the ophthalmic pharmaceutical composition of the present invention comprises L-lysine, e.g., L-lysine HCL (e.g., a first therapeutic agent). In some embodiments, the L-lysine is a free amino acid. In some embodiments, L-lysine is a part of a peptide, e.g., a multimer of lysine or a peptide with one or more other amino acids. For example, in some embodiments, the formulation comprises a peptide, wherein one or more amino acids of the peptide is lysine. The structure of L-lysine is shown below.

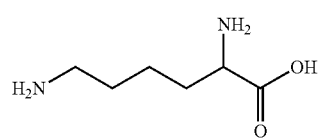

In some embodiments, L-lysine (e.g., as a first or second therapeutic agent) in ophthalmic formulations may be present at a concentration ranging from about 1% to 5% w/v (e.g., g/100 mL). In certain embodiments, the concentration of L-lysine may be approximately 3% w/v.

In some embodiments, L-lysine (e.g., as a first or second therapeutic agent) in ophthalmic formulations may be present at a concentration ranging from about 0.001% to 0.999% w/v. In some embodiments, L-lysine (e.g., as a first or second therapeutic agent) in ophthalmic formulations may be present at a concentration ranging from about 0.1% to 10% w/v, or about 0.1% to 8% w/v, or about 0.1% to 6% w/v, or about 0.1% to 5% w/v, or about 0.1% to 4% w/v, or about 0.1% to 3% w/v, or about 0.1% to 2% w/v or about 0.1% to 1% w/v. In some embodiments, L-lysine (e.g., as a first or second therapeutic agent) in ophthalmic formulations may be present at a concentration ranging from about 0.25% to 10% w/v, or about 0.25% to 8% w/v, or about 0.25% to 6% w/v, or about 0.25% to 5% w/v, or about 0.25% to 4% w/v, or about 0.25% to 3% w/v, or about 0.25% to 2% w/v or about 0.25% to 1% w/v.

In some embodiments, L-lysine (e.g., as a first or second therapeutic agent) in ophthalmic formulations may be present at a concentration ranging from about 0.5% to 10% w/v, or about 0.5% to 8% w/v, or about 0.5% to 6% w/v, or about 0.5% to 5% w/v, or about 0.5% to 4% w/v, or about 0.5% to 3% w/v, or about 0.5% to 2% w/v or about 0.5% to 1% w/v. In some embodiments, L-lysine (e.g., as a first or second therapeutic agent) in ophthalmic formulations may be present at a concentration ranging from about 1% to 10% w/v, or about 1% to 8% w/v, or about 1% to 6% w/v, or about 1% to 5% w/v, or about 1% to 4% w/v, or about 1% to 3% w/v.

In some embodiments, L-lysine (e.g., as a first or second therapeutic agent) in ophthalmic formulations may be present at a concentration ranging from about 5% to 10% w/v. In some embodiments, L-lysine (e.g., as a first or second therapeutic agent) in ophthalmic formulations may be present at a concentration ranging from about 10% to 15% w/v. In some embodiments, L-lysine (e.g., as a first or second therapeutic agent) in ophthalmic formulations may be present at a concentration ranging from about 15% to 20% w/v. In some embodiments, L-lysine (e.g., as a first or second therapeutic agent) in ophthalmic formulations may be present at a concentration ranging from about 20% to 25% w/v. In some embodiments, L-lysine (e.g., as a first or second therapeutic agent) in ophthalmic formulations may be present at a concentration ranging from about 25% to 30% w/v. In some embodiments, L-lysine (e.g., as a first or second therapeutic agent) in ophthalmic formulations may be present at a concentration ranging from about 30% to 35% w/v.

In some embodiments, ligustilide (e.g., as a first or second therapeutic agent) in ophthalmic formulations may be present at a concentration ranging from about 1% to 10% w/v (e.g., g/100 mL). In some embodiments, ligustilide (e.g., as a first or second therapeutic agent) in ophthalmic formulations may be present at a concentration ranging from about 3% to 6% w/v (e.g., g/100 mL). In certain embodiments, the concentration of ligustilide may be approximately 5% w/v.

In some embodiments, the ophthalmic pharmaceutical composition of the present invention comprises ligustilide (e.g., a first therapeutic agent). In other embodiments, the ophthalmic pharmaceutical composition of the present invention comprises ligustilide extracted from *Ligusticum porteri* (Osha root). In further embodiments, the ophthalmic pharmaceutical composition of the present invention comprises ligustilide extracted from *Angelica sinensis* (dong quai or Female *ginseng*). In some embodiments, the ophthalmic pharmaceutical composition of the present invention comprises Osha root extract, e.g., that comprises ligustilide. In other embodiments, the ophthalmic pharmaceutical composition of the present invention comprises Female *ginseng* extract, e.g., that comprises ligustilide.

In some embodiments, the ophthalmic formulations (or ophthalmic pharmaceutical composition) may comprise either z-ligustilide, e-ligustilide, or both z-ligustilide and e-ligustilide. Without wishing to limit the present invention to any theory or mechanism, it is believed that the Z-isomer exhibits significantly greater structural stability compared to the E-isomer, with each isomer possessing distinct structural and pharmacological properties. For example, the Z-isomer demonstrates antioxidant, anti-inflammatory, and neuroprotective effects, whereas the E-isomer inhibits cell proliferation and migration while also exhibiting anti-inflammatory activity.

In some embodiments, the ligustilide (e.g., as a first or second therapeutic agent) in ophthalmic formulations may be present at a concentration ranging from about 0.001% to 0.999% w/v. In some embodiments, ligustilide (e.g., as a first or second therapeutic agent) in ophthalmic formulations may be present at a concentration ranging from about 0.001% to 0.999% w/v. In some embodiments, ligustilide (e.g., as a first or second therapeutic agent) in ophthalmic formulations may be present at a concentration ranging from about 0.1% to 15% w/v, or about 0.1% to 10% w/v, or about 0.1% to 9% w/v, or about 0.1% to 8% w/v, or about 0.1% to 7% w/v, or about 0.1% to 6% w/v, or about 0.1% to 5% w/v, or about 0.1% to 4% w/v, or about 0.1% to 3% w/v, or about 0.1% to 2% w/v, or about 0.1% to 1% w/v.

In some embodiments, ligustilide (e.g., as a first or second therapeutic agent) in ophthalmic formulations may be present at a concentration ranging from about 1% to 15% w/v, or about 1% to 10% w/v, or about 1% to 9% w/v, or about 1% to 8% w/v, or about 1% to 7% w/v, or about 1% to 6% w/v, or about 1% to 5% w/v, or about 1% to 4% w/v, or about 1% to 3% w/v, or about 1% to 2% w/v. In some embodiments, ligustilide (e.g., as a first or second therapeutic agent) in ophthalmic formulations may be present at a concentration ranging from about 3% to 15% w/v, or about 3% to 10% w/v, or about 3% to 9% w/v, or about 3% to 8% w/v, or about 3% to 7% w/V, or about 3% to 6% w/v, or about 3% to 5% w/v, or about 3% to 4% w/v.

In some embodiments, ligustilide (e.g., as a first or second therapeutic agent) in ophthalmic formulations may be present at a concentration ranging from about 10% to 15%. In some embodiments, ligustilide (e.g., as a first or second therapeutic agent) in ophthalmic formulations may be present at a concentration ranging from about 15% to 20%. In some embodiments, ligustilide (e.g., as a first or second therapeutic agent) in ophthalmic formulations may be present at a concentration ranging from about 20% to 25%. In some embodiments, ligustilide (e.g., as a first or second therapeutic agent) in ophthalmic formulations may be present at a concentration ranging from about 25% to 30%. In some embodiments, ligustilide (e.g., as a first or second therapeutic agent) in ophthalmic formulations may be present at a concentration ranging from about 30% to 35%.

In certain embodiments, the present invention features a topical ophthalmic formulation comprising about 1% to 10% w/v ligustilide (e.g., a first therapeutic agent), e.g., extracted from Osha root, and 1% to 5% L-lysine (e.g., a second therapeutic agent). In certain embodiments, the present invention features a topical ophthalmic formulation comprising about 1% to 5% w/v L-lysine (e.g., a first therapeutic agent), e.g., extracted from Osha root, and 1% to 10% ligustilide (e.g., a second therapeutic agent). In certain embodiments, the present invention features a topical ophthalmic formulation comprising about 5% ligustilide (or Osha root extract) and 3% L-lysine. However, the present invention is not restricted to the concentrations of the first or second therapeutic agents specified above and may encompass any of the concentrations listed in Table 3. In some embodiments, the formulation is an aqueous formulation, such as eye drops.

The pharmaceutical composition of the present invention is not limited to the combination of L-lysine and ligustilide. Approximately 154 naturally occurring compounds have been identified in Osha root, e.g., extracts of osha root. Phthalides comprise >50% of these compounds; the remaining compounds are terpenoids, steroids, alkaloids, organics acids, saccharides, ceramides, and cerebrosides. Five secondary metabolites that have bioactivity are z-ligustilide, transferulic acid, z/e-3-butylidenephthalide, isovanillin, and elemicin. Table 1 shows forty-two of the major compounds comprising approximately 88.1% of all identifiable compounds derived from Osha root (adapted from Cegiela-Carlioz et al., 2005).

TABLE 1

| No. | Compound | Essential oil % |
|---|---|---|
| 1 | alpha-thujene | 0.05 |
| 2 | alpha-pinene | 0.1 |
| 3 | sabinene | 0.4 |
| 4 | beta-pinene | 0.3 |
| 5 | myrcene | 0.1 |
| 6 | alpha-phellandrene | 0.3 |
| 7 | alpha-terpinene | 0.2 |
| 8 | rho-cymene | 0.9 |
| 9 | beta-phellandrene | 0.4 |
| 10 | limonine | 0.1 |
| 11 | gamma-terpinene | 0.3 |
| 12 | cis-thujone | 0.03 |
| 13 | 1,3,8 menthatriene | 0.1 |
| 14 | alpha-phellandrene 1,2 epoxide | 1.9 |
| 15 | sabinol | 3.3 |
| 16 | pentylbenzene | 2.1 |
| 17 | terpinen-4-ol | 0.8 |
| 18 | alpha-terpineol | 0.1 |
| 19 | thymyl methylether | 0.05 |
| 20 | carvacryl methylether | 0.9 |
| 21 | isothujyl acetate | 0.2 |
| 22 | trans-pinocarveyl acetate | 0.1 |
| 23 | bornyl acetate | 1.8 |
| 24 | sabinyl acetate | 56.6 |
| 25 | 4-vinylguaiacol | 0.4 |
| 26 | 4-terpinyl acetate | 0.1 |
| 27 | alpha-terpinyl acetate | 1.3 |
| 28 | o-methyleugenol | 1.1 |
| 29 | 2,5-dimethoxy-rho-cymene | 0.3 |
| 30 | alpha-barbatene | 0.3 |
| 31 | beta-funebrene | 0.1 |
| 32 | widdrene | 0.2 |
| 33 | beta-barbatene | 1.3 |
| 34 | myristicin | 0.8 |
| 35 | (-)-kessane | 0.6 |
| 36 | liguloxide | 0.5 |
| 37 | alpha-chamigrene | — |
| 38 | elemicin | 0.5 |
| 39 | (z)-3-butylidenephthalide | 0.8 |
| 40 | alpha-eudesmol | 0.2 |
| 41 | (z)-ligustilide | 12.9 |
| 42 | (e)-ligustilide | 0.2 |

As previously discussed, the present invention is not limited to ophthalmic formulations comprising a first therapeutic agent and/or a second therapeutic agent. For example, the present invention may feature an ophthalmic formulation comprising a first therapeutic agent comprising L-lysine, a second therapeutic agent comprising ligustilide as the second therapeutic agent, and a third therapeutic agent. Optionally, the ophthalmic formulation may further comprise a fourth therapeutic agent. In some embodiments, the second therapeutic agent comprises osha root extract, e.g., as described herein.

In some embodiments, the first therapeutic agent is ligustilide. In some embodiments, the first therapeutic agent is osha root extract. In some embodiments, the first therapeutic agent is Female *ginseng* extract. In other embodiments, the first therapeutic agent is L-lysine.

Embodiments in which ligustilide serves as the first therapeutic agent may further include a second therapeutic agent, such as L-lysine. Alternatively, embodiments in which L-lysine serves as the first therapeutic agent may further include a second therapeutic agent, such as ligustilide (e.g., extracted either from Osha Root or Female *ginseng*).

In some embodiments, the second therapeutic agent is an antihistamine, an anti-inflammatory agent, an immunosuppressive agent, a steroid, an antiviral agent, an antimycotic agent, or an anti-allergic agent. Additionally, in some embodiments, the aforementioned formulations may further comprise a third or fourth therapeutic agent. For example, the third or fourth therapeutic agent may comprise an antihistamine, an anti-inflammatory agent, an immunosuppressive agent, a steroid, an antiviral agent, an antimycotic agent, or an anti-allergic agent.

Further, the pharmaceutical composition of the present invention may comprise a third therapeutic agent. The pharmaceutical composition may comprise a fourth therapeutic agent or more than four therapeutic agents.

In certain embodiments, the second therapeutic agent or third therapeutic agent, or fourth therapeutic agent comprises an antihistamine, e.g., a first generation antihistamine (e.g., diphenhydramine, brompheniramine, chlorpheniramine, pheniramine, etc.), or a second generation antihistamine (e.g., loratadine, cetirizine, fexofenadine, desloratadine, levocetirizine, alcaftadine, etc.), or a derivative thereof, or a combination thereof.

In some embodiments, the second therapeutic agent, the third therapeutic agent, or the fourth therapeutic agent comprises an anti-inflammatory agent (e.g., ketorolac, bromfenac, diclofenac, flurbiprofen, nepafenac, lifitegrast, etc.), or a derivative thereof, or a combination thereof.

In some embodiments, the second therapeutic agent, the third therapeutic agent, or the fourth therapeutic agent comprises an immunosuppressive agent (e.g., cyclosporine, tacrolimus, etc.) or a derivative thereof. Non-limiting examples of immunosuppressive agents may also include but are not limited to chemokine receptor antagonists, colony-stimulating factor-1 receptor inhibitors, complement inhibitors, interleukin antagonists, JAK inhibitors, TNF inhibitors. The present invention is not limited to the immunosuppressive agents mentioned above and may encompass additional agents in accordance with the scope of the invention.

In some embodiments, the second therapeutic agent, the third therapeutic agent, or the fourth therapeutic agent comprises a steroid. Non-limiting examples of steroids that may be used include difluprednate (durezol), prednisolone, dexamethasone, fluocinolone, loteprednol, triamcinolone, fluorometholone, beta-methasone, corticosterone, etc. or a derivative thereof, or a combination thereof. The present invention is not limited to the aforementioned steroids and may encompass additional compounds within the scope of the invention.

In some embodiments, the second therapeutic agent, the third therapeutic agent, or the fourth therapeutic agent comprises an antiviral agent. Non-limiting examples of antiviral agents may include but are not limited to valacyclovir, penciclovir, famciclovir, foscarnet, acyclovir, ganciclovir, trifluridine, or a derivative thereof, or a combination thereof. The present invention is not limited to the antiviral agents mentioned above and may encompass additional agents in accordance with the scope of the invention.

In some embodiments, the second therapeutic agent, the third therapeutic agent, or the fourth therapeutic agent comprises an antimycotic agent. Non-limiting examples of antimycotic agents may include but are not limited to terbinafine, natamycin, voriconazole, echinocandines, pimaricin, fluconazole, miconazole, amphotericin B, flucytosine, itraconazole, etc., or a derivative thereof, or a combination thereof. The present invention is not limited to the antimycotic agents mentioned above and may encompass additional agents in accordance with the scope of the invention.

In some embodiments, the second therapeutic agent, the third therapeutic agent, or fourth therapeutic agent comprises an anti-allergic agent. Non-limiting examples of anti-allergic agents that may be used include but are not limited to cetirizine, loratadine, fexofenadine, levocetirizine, desloratadine, tranilast, ketotifen fumarate, diphenhydramine hydrochloride, sodium cromoglicate, etc., or a derivative thereof, or a combination thereof. The present invention is not limited to the anti-allergic agents mentioned above and may encompass additional agents in accordance with the scope of the invention.

In some embodiments, the selection of the second, third, and fourth therapeutic agents may be based on the subject's diagnosis, such as FHV-1 in combination with dry eyes, conjunctivitis, fungal keratitis, or iridocyclitis. For example, FHV-1 viral keratitis can create conditions on the corneal surface that are conducive to superinfection with bacterial or fungal pathogens. In chronic cases of FHV-1, particularly in feral animals lacking access to treatment, various fungal infections may develop alongside the underlying viral keratitis. In such instances, an antimycotic agent (e.g., natamycin may be administered initially, with adjustments made based on biopsy sensitivity.) combined with the compositions described herein (e.g., ligustilide extracted from Osha root and L-lysine) would not only address the underlying viral infection but also effectively treat the fungal superinfection.

Table 2 below shows non-limiting examples of pharmaceutical compositions. The pharmaceutical compositions in Table 2 comprise L-lysine and one or more additional agents. In some embodiments, the formulations comprise a combination of two or more compositions within the category (e.g., a combination of two immunosuppressive agents, e.g., a combination of cyclosporine and tacrolimus, e.g., cyclosporine 1% drops or 0.2% ointment+tacrolimus 0.2%). Note in Table 2 "ligustilide" may refer to osha root extract.

| Example | L-lysine | Ligustilide | Anti-histamine | Anti-inflammatory agent | Immuno-suppressive agent | Steroid | Anti-viral agent | Anti-mycotic agent | Anti-allergic agent |
|---|---|---|---|---|---|---|---|---|---|
| 1 | X | X | X | | | | | | |
| 2 | X | X | | X | | | | | |
| 3 | X | X | | | X | | | | |
| 4 | X | X | | | | X | | | |
| 5 | X | X | | | | | X | | |
| 6 | X | X | | | | | | X | |
| 7 | X | X | | | | | | | X |
| 8 | X | X | X | X | | | | | |
| 9 | X | X | X | | X | | | | |
| 10 | X | X | X | | | X | | | |
| 11 | X | X | X | | | | X | | |
| 12 | X | X | X | | | | | X | |
| 13 | X | X | X | | | | | | X |
| 14 | X | X | | X | X | | | | |
| 15 | X | X | | X | | X | | | |
| 16 | X | X | | X | | | X | | |
| 17 | X | X | | X | | | | X | |
| 18 | X | X | | X | | | | | X |
| 19 | X | X | | | X | X | | | |
| 20 | X | X | | | X | | X | | |
| 21 | X | X | | | X | | | X | |
| 22 | X | X | | | X | | | | X |
| 23 | X | X | | | | X | X | | |
| 24 | X | X | | | | X | | X | |
| 25 | X | X | | | | X | | | X |
| 26 | X | X | | | | | X | X | |
| 27 | X | X | | | | | X | | X |
| 28 | X | X | | | | | | X | X |
| 29 | X | X | X | X | X | | | | |
| 30 | X | X | X | X | | X | | | |
| 31 | X | X | X | X | | | X | | |
| 32 | X | X | X | X | | | | X | |
| 33 | X | X | X | X | | | | | X |
| 34 | X | X | X | | X | X | | | |
| 35 | X | X | X | | X | | X | | |
| 36 | X | X | X | | X | | | X | |
| 37 | X | X | X | | X | | | | X |
| 38 | X | X | X | | | X | X | | |
| 39 | X | X | X | | | X | | X | |
| 40 | X | X | X | | | X | | | X |

-continued

| Example | L-lysine | Ligustilide | Anti-histamine | Anti-inflammatory agent | Immuno-suppressive agent | Steroid | Anti-viral agent | Anti-mycotic agent | Anti-allergic agent |
|---|---|---|---|---|---|---|---|---|---|
| 41 | X | X | X | | | | X | X | |
| 42 | X | X | X | | | | X | | X |
| 43 | X | X | X | | | | | X | X |
| 44 | X | X | | X | X | X | | | |
| 45 | X | X | | X | X | | X | | |
| 46 | X | X | | X | X | | | X | |
| 47 | X | X | | X | X | | | | X |
| 48 | X | X | | X | | | X | X | |
| 49 | X | X | | X | | | X | X | |
| 50 | X | X | | X | | | X | | X |
| 51 | X | X | | X | | | X | X | |
| 52 | X | X | | X | | | X | | X |
| 53 | X | X | | X | | | | X | X |
| 54 | X | X | | | X | X | X | | |
| 55 | X | X | | | X | X | | X | |
| 56 | X | X | | | X | X | | | X |
| 57 | X | X | | | X | | X | X | |
| 58 | X | X | | | X | | X | | X |
| 59 | X | X | | | X | | | X | X |
| 60 | X | X | | | | | X | X | |
| 61 | X | X | | | | | X | X | X |
| 62 | X | X | | | | | X | X | X |
| 63 | X | X | | | | | X | X | X |
| 64 | X | | X | | | | | | |
| 65 | X | | | X | | | | | |
| 66 | X | | | | X | | | | |
| 67 | X | | | | | X | | | |
| 68 | X | | | | | | X | | |
| 69 | X | | | | | | | X | |
| 70 | X | | | | | | | | X |
| 71 | X | | X | X | | | | | |
| 72 | X | | X | | X | | | | |
| 73 | X | | X | | | X | | | |
| 74 | X | | X | | | | X | | |
| 75 | X | | X | | | | | X | |
| 76 | X | | X | | | | | | X |
| 77 | X | | | X | X | | | | |
| 78 | X | | | X | | X | | | |
| 79 | X | | | X | | | X | | |
| 80 | X | | | X | | | | X | |
| 81 | X | | | X | | | | | X |
| 82 | X | | | | X | X | | | |
| 83 | X | | | | X | | X | | |
| 84 | X | | | | X | | | X | |
| 85 | X | | | | X | | | | X |
| 86 | X | | | | | | X | X | |
| 87 | X | | | | | | X | X | |
| 88 | X | | | | | | X | | X |
| 89 | X | | | | | | X | X | |
| 90 | X | | | | | | X | | X |
| 91 | X | | | | | | | X | X |
| 92 | X | | X | X | X | | | | |
| 93 | X | | X | X | | X | | | |
| 94 | X | | X | X | | | X | | |
| 95 | X | | X | X | | | | X | |
| 96 | X | | X | X | | | | | X |
| 97 | X | | X | | X | X | | | |
| 98 | X | | X | | X | | X | | |
| 99 | X | | X | | X | | | X | |
| 100 | X | | X | | X | | | | X |
| 101 | X | | X | | | | X | X | |
| 102 | X | | X | | | | X | X | |
| 103 | X | | X | | | | X | | X |
| 104 | X | | X | | | | X | X | |
| 105 | X | | X | | | | X | | X |
| 106 | X | | X | | | | | X | X |
| 107 | X | | | X | X | X | | | |
| 108 | X | | | X | X | | X | | |
| 109 | X | | | X | X | | | X | |
| 110 | X | | | X | X | | | | X |
| 111 | X | | | X | | | X | X | |
| 112 | X | | | X | | | X | | X |
| 113 | X | | | X | | | X | | X |
| 114 | X | | | X | | | X | X | |
| 115 | X | | | X | | | X | | X |

| Example | L-lysine | Ligustilide | Anti-histamine | Anti-inflammatory agent | Immuno-suppressive agent | Steroid | Anti-viral agent | Anti-mycotic agent | Anti-allergic agent |
|---|---|---|---|---|---|---|---|---|---|
| 116 | X | | | X | | | | X | X |
| 117 | X | | | | X | X | X | | |
| 118 | X | | | | X | X | | X | |
| 119 | X | | | | X | X | | | X |
| 120 | X | | | | X | | X | X | |
| 121 | X | | | | X | | X | | X |
| 122 | X | | | | X | | | X | X |
| 123 | X | | | | | X | X | X | |
| 124 | X | | | | | X | X | | X |
| 125 | X | | | | | X | | X | X |
| 126 | X | | | | | | X | X | X |

Table 3 below provides additional non-limiting examples of pharmaceutical compositions of the present invention.

TABLE 3

| Example | Pharmaceutical Composition (% = % w/v, e.g., g/100 mL) |
|---|---|
| 127 | 0.1% L-lysine |
| 128 | 0.5% L-lysine |
| 129 | 1% L-lysine |
| 130 | 2% L-lysine |
| 131 | 3% L-lysine |
| 132 | 4% L-lysine |
| 133 | 5% L-lysine |
| 134 | 6% L-lysine |
| 135 | 7% L-lysine |
| 136 | 8% L-lysine |
| 137 | 9% L-lysine |
| 138 | 10% L-lysine |
| 139 | 2% L-lysine / 4% Ligustilide |
| 140 | 2% L-lysine / 5% Ligustilide |
| 141 | 2% L-lysine / 6% Ligustilide |
| 142 | 3% L-lysine / 2% Ligustilide |
| 143 | 3% L-lysine / 3% Ligustilide |
| 144 | 3% L-lysine / 5% Ligustilide |
| 145 | 3% L-lysine / 8% Ligustilide |
| 146 | 3% L-lysine / 10% Ligustilide |
| 147 | 5% L-lysine / 1% Ligustilide |
| 148 | 5% L-lysine / 2% Ligustilide |
| 149 | 5% L-lysine / 3% Ligustilide |
| 150 | 5% L-lysine / 4% Ligustilide |
| 151 | 5% L-lysine / 5% Ligustilide |
| 152 | 5% L-lysine / 8% Ligustilide |
| 153 | 5% L-lysine / 10% Ligustilide |
| 154 | 6% L-lysine / 2% Ligustilide |
| 155 | 6% L-lysine / 3% Ligustilide |
| 156 | 6% L-lysine / 4% Ligustilide |
| 157 | 6% L-lysine / 5% Ligustilide |
| 158 | 6% L-lysine / 6% Ligustilide |
| 159 | 3% L-lysine / 20% Ligustilide |
| 160 | 5% L-lysine / 20% ligustilide |
| 161 | 3% L-lysine / 30% Ligustilide |
| 162 | 5% L-lysine / 30% Ligustilide |
| 163 | 3% L-lysine / 40% Ligustilide |
| 164 | 5% L-lysine / 40% Ligustilide |
| 165 | 3% L-lysine / 50% Ligustilide |
| 166 | 5% L-lysine / 50% Ligustilide |
| 167 | 2% L-lysine / 4% Osha Root Extract |
| 168 | 2% L-lysine / 5% Osha Root Extract |
| 169 | 2% L-lysine / 6% Osha Root Extract |
| 170 | 3% L-lysine / 4% Osha Root Extract |
| 171 | 3% L-lysine / 5% Osha Root Extract |
| 172 | 3% L-lysine / 6% Osha Root Extract |
| 173 | 5% L-lysine / 4% Osha Root Extract |
| 174 | 5% L-lysine / 5% Osha Root Extract |
| 175 | 5% L-lysine / 6% Osha Root Extract |
| 176 | 0.1% Ligustilide |
| 177 | 0.5% Ligustilide |
| 178 | 1% Ligustilide |
| 179 | 2% Ligustilide |
| 180 | 3% Ligustilide |
| 181 | 4% Ligustilide |
| 182 | 5% Ligustilide |
| 183 | 6% Ligustilide |
| 184 | 7% Ligustilide |
| 185 | 8% Ligustilide |
| 186 | 9% Ligustilide |
| 187 | 10% Ligustilide |
| 188 | 2% Ligustilide / 4% L-lysine |
| 189 | 2% Ligustilide / 5% L-lysine |
| 190 | 2% Ligustilide / 6% L-lysine |
| 191 | 3% Ligustilide / 2% L-lysine |

TABLE 3-continued

| Example | Pharmaceutical Composition (% = % w/v, e.g., g/100 mL) |
|---|---|
| 192 | 3% Ligustilide<br>5% L-lysine |
| 193 | 3% Ligustilide<br>8% L-lysine |
| 194 | 3% Ligustilide<br>10% L-lysine |
| 195 | 5% Ligustilide<br>1% L-lysine |
| 196 | 5% Ligustilide<br>2% L-lysine |
| 197 | 5% Ligustilide<br>3% L-lysine |
| 198 | 5% Ligustilide<br>4% L-lysine |
| 199 | 5% Ligustilide<br>8% L-lysine |
| 200 | 5% Ligustilide<br>10% L-lysine |
| 201 | 6% Ligustilide<br>2% L-lysine |
| 202 | 6% Ligustilide<br>3% L-lysine |
| 203 | 6% Ligustilide<br>4% L-lysine |
| 204 | 6% Ligustilide<br>5% L-lysine |
| 205 | 3% Ligustilide<br>20% L-lysine |
| 206 | 5% Ligustilide<br>20% L-lysine |
| 207 | 3% Ligustilide<br>30% L-lysine |
| 208 | 5% Ligustilide<br>30% L-lysine |
| 209 | 3% Ligustilide<br>40% L-lysine |
| 210 | 5% Ligustilide<br>40% L-lysine |
| 211 | 3% Ligustilide<br>50% L-lysine |
| 212 | 5% Ligustilide<br>50% L-lysine |
| 213 | 2% Osha Root Extract<br>4% L-lysine |
| 214 | 2% Osha Root Extract<br>5% L-lysine |
| 215 | 2% Osha Root Extract<br>6% L-lysine |
| 216 | 3% Osha Root Extract<br>4% L-lysine |
| 217 | 3% Osha Root Extract<br>5% L-lysine |
| 218 | 3% Osha Root Extract<br>6% L-lysine |
| 219 | 5% Osha Root Extract<br>4% L-lysine |
| 220 | 5% Osha Root Extract<br>6% L-lysine |
| 221 | 3% L-lysine<br>10% Osha Root Extract |
| 222 | 3% L-lysine<br>25% Osha Root Extract |
| 223 | 5% Osha Root Extract<br>10% L-lysine |
| 224 | 5% Osha Root Extract<br>25% L-lysine |

In some embodiments, the pharmaceutical composition comprises bacteriostatic water, bacteriostatic saline (e.g., NaCl 0.9%), polyethylene glycol, polyvinyl alcohol (e.g., 0.5%), propylene glycol, povidone (e.g., 0.6%), glycerine, mineral oil, a demulcent (e.g., carboxymethylcellulose, hydroxyethyl cellulose, hypromellose, methylcellulose, etc.), a derivative thereof, or a combination thereof.

The ophthalmic formulations of the present invention may also comprise a buffer or buffer system. Buffers, such as those used for ophthalmic applications, are well known to one of ordinary skill in the art. As used herein, the terms "buffer" or "buffer system" refer to a compound that, usually in combination with at least one other compound, provides a solution that exhibits buffering capacity, e.g., the capacity to neutralize, within limits, either acids or bases with relatively little or no change in the original pH. A non-limiting example of a buffer includes a balanced salt solution (BSS). The present invention is not limited to BSS and includes any appropriate buffer to be appropriately used as a substitute for BSS, hydrochloric acid (HCl), sodium bicarbonate ($NaHCO_3$), citrate, phosphate, Tris-HCl (Tris), borate (boric acid), etc.

In some embodiments, the pH of the ophthalmic solution is at or near physiological pH. For example, in some embodiments, the pH of the aqueous ophthalmic solution is between about 6.8 to about 7.85 (e.g., about 6.8, about 6.9, about 7.0, about 7.1, about 7.2, about 7.3, about 7.4, about 7.5, about 7.6, or about 7.7, or about 7.85). In some embodiments, the pH of the aqueous ophthalmic solution is between about 6.8 to about 7.85. In some embodiments, the pH of the aqueous ophthalmic solution is between about 6.8 to about 7.4. In some embodiments, the pH of the aqueous ophthalmic solution is between about 7.0 to about 7.4. In some embodiments, the pH of the aqueous ophthalmic solution is between about 7.2 to about 7.4. In some embodiments, the pH of the aqueous ophthalmic solution is between about 7.2 to about 7.5.

In certain embodiments, the ophthalmic solution is formulated to a specific osmolarity. Without wishing to limit the present invention to any theory or mechanism, it is believed that the osmolarity of the ophthalmic solution may significantly influence the properties of the treated tissue, such as absorption and diffusion. Accordingly, in some embodiments, the present invention features three variations of osmolarity iso-osmolar (290-320 mOsm/kg), hypo-osmolar (135-165 mOsm/kg), and hyper-osmolar (greater than 320 mOsm/kg).

For example, an iso-osmolar solution may be used in ocular preparations as it closely mimics the osmolarity of normal tear fluid. Hypo-osmolar solutions (i.e., those with an osmolarity of less than 300 mOsm/kg) may be used in the treatment of dry eye and other inflammatory conditions by enhancing hydration of the corneal surface and facilitating tissue penetration. Conversely, hyper-osmolar solutions may mitigate corneal and conjunctival edema by utilizing hydrostatic pressure to extract fluid from the tissues. However, hyper-osmolar tears are also frequently observed in inflammatory states such as dry eye or infections, serving as an indicator of disease. Thus, there may be potential utility in hyper-osmolar solutions for the replacement or repair of tissue damage associated with various inflammatory conditions, including corneal and conjunctival edema.

Under normal physiological conditions, mean tear osmolality values for both humans and felines are relatively consistent, typically ranging between 290 and 315 mOsm/kg.

In some embodiments, an iso-osmolar formulation is used to eliminate osmolar gradients, ensuring that water remains neutral. This allows the components (e.g., ingredients) of the solution to diffuse along their respective concentration gradients into or out of tissues. Most ophthalmic preparations are designed to be iso-osmolar to prevent swelling and enhance patient comfort. Without wishing to limit the present invention to any theory or mechanism, it is believed that since tears drain into the nasopharyngeal space, sinus or upper respiratory conditions, such as allergic rhinitis or sinusitis, can be treated through an ophthalmic route of administration. Furthermore, this approach may be utilized to treat conditions such as keratitis or intraocular inflammation, including iridocyclitis.

The ophthalmic formulation may be manufactured as an aqueous formulation, e.g., aqueous eye drops, aqueous suspension eye drops, viscous eye drops, or solubilized eye drops. In some embodiments, the formulation is manufactured as a non-aqueous formulation, such as non-aqueous eye drops and non-aqueous suspension eye drops or an ophthalmic gel, ointment, or spray.

In some embodiments, the ophthalmic formulation comprises a suspending agent (e.g., polyvinyl pyrrolidone, glycerin monostearate, sorbitan esters, and lanolin alcohols). In some embodiments, the ophthalmic formulation comprises a dispersing agent (e.g., surfactants such as tyloxapol and polysorbate 80, ionic polymers such as sodium alginate). The suspending agent and/or dispersing agent may help to ensure that the ophthalmic formulation is satisfactorily dispersed in a uniform microparticulate suspension.

The formulation may comprise one or more excipients incorporated ordinarily, such as buffering agents (e.g., phosphate buffers, borate buffers, citrate buffers, tartrate buffers, acetate buffers, amino acids, sodium acetate, sodium citrate and the like), isotonicity agents (e.g., saccharides such as but not limited to sorbitol, glucose and mannitol, polyhydric alcohols such as but not limited to glycerin, concentrated glycerin, polyethylene glycol and propylene glycol, salts such as but not limited to sodium chloride), preservatives or antiseptics (e.g., benzalkonium chloride (BAK), polidronium chloride (D-polyquaternium-1 or polyQuad), benzethonium chloride, p-oxybenzoates such as but not limited to methyl p-oxybenzoate or ethyl p-oxybenzoate, benzyl alcohol, phenethyl alcohol, sorbic acid or its salt, thimerosal, chlorobutanol, other quaternary amines and the like), solubilizing aids or stabilizing agents (e.g., cyclodextrins and their derivatives, water-soluble polymers such as polyvinyl pyrrolidone, or carbomer, surfactants such as polysorbate 80, pH modifiers (e.g., hydrochloric acid, acetic acid, phosphoric acid, sodium hydroxide, potassium hydroxide, ammonium hydroxide and the like), thickening agents (e.g., hydroxyethyl cellulose, hydroxypropyl cellulose, methyl cellulose, hydroxypropylmethyl cellulose, carboxymethyl cellulose and their salts), chelating agents (e.g., sodium edetate, sodium citrate, condensed sodium phosphate) and the like. Non-limiting examples of the contemplated excipients include a buffer, osmotic agent, demulcent, surfactant, emollient, tonicity agent, and/or a preservative component. The aforementioned compounds are well known to be an ordinary skill in the art and are used in standard ophthalmic formulations.

The formulation of the present invention may be mixed with a pharmaceutically (e.g., ophthalmically) acceptable carrier, excipient, or diluent.

In some embodiments, the pharmaceutical composition is manufactured with preservatives. In some embodiments, the pharmaceutical composition is manufactured without preservatives.

The composition of the present invention may be manufactured in packaging appropriate for its particular formulation. For example, a liquid formulation may be packaged in a single-dose package (e.g., blister package) or a multi-dose package, e.g., bottle dispenser or droppers. In some embodiments, the packaging features a dispensing system wherein the liquid formulation passes through a filter to prevent microbial contamination.

Administration, Methods of Treatment, and Dosing

The present invention also features methods of treating, managing, ameliorating, and/or preventing FHV infection in cats. The methods herein include ameliorating or alleviating symptoms associated with FHV infection in cats. The methods feature administering a therapeutically effective amount of a pharmaceutical composition, e.g., an ophthalmic formulation, according to the present invention, e.g., a formulation comprising L-lysine, a formulation comprising L-lysine and a second therapeutic agent such as but not limited to ligustilide.

The present invention may also feature a pharmaceutical composition for use in a method of treating, managing, ameliorating, and/or preventing FHV infection in cats. In some embodiments, the pharmaceutical compositions comprises ligustilide (e.g., a first therapeutic agent), e.g., extracted from Osha root, and a second therapeutic agent (e.g., a second therapeutic agent comprising L-lysine). In other embodiments, the pharmaceutical compositions comprises L-lysine (e.g., a first therapeutic agent) and a second therapeutic agent (e.g., a second therapeutic agent comprising ligustilide).

As described above, the pharmaceutical composition of the present invention may be manufactured as a topical agent, e.g., in the form of drops, an ointment, a gel, a spray, etc. The pharmaceutical composition is administered in a manner consistent with the formulation of the pharmaceutical composition.

In one aspect of the present invention, the pharmaceutical composition is manufactured for use in cats.

In one aspect of the present invention, the pharmaceutical composition is manufactured for use in humans.

In one aspect of the present invention, the pharmaceutical composition is manufactured for use in dogs or other animals.

In some embodiments, the formulation is administered once a day (e.g., to one eye one time in a day or to both eyes one time in a day). In some embodiments, the formulation is administered twice a day (e.g., to one eye twice in a day or to both eyes twice in a day). In some embodiments, the formulation is administered three times a day (e.g., to one eye three times in a day or to both eyes three times in a day). In some embodiments, the formulation is administered four times a day (e.g., to one eye four times in a day or to both eyes four times in a day). In some embodiments, the formulation is administered more than four times a day.

In some embodiments, the formulation is administered one or more times (to one or both eyes) over a period of one day. In some embodiments, the formulation is administered one or more times (to one or both eyes) over a period of two days. In some embodiments, the formulation is administered one or more times (to one or both eyes) over a period of three days. In some embodiments, the formulation is administered one or more times (to one or both eyes) over a period of four days. In some embodiments, the formulation is administered one or more times (to one or both eyes) over a period of five days. In some embodiments, the formulation is administered one or more times (to one or both eyes) over a period of six days. In some embodiments, the formulation is administered one or more times (to one or both eyes) over a period of seven days. In some embodiments, the formulation is administered one or more times (to one or both eyes) over a period of more than seven days. The frequency of administration and/or the duration of the treatment may depend on the symptoms of the disease and may vary day by day.

As previously discussed, treating of FHV may require the administration of treatments throughout the lifetime of the animal. In particular, treatments may be required during periods of stress, e.g., illness, stress in the home environment, attending veterinarian appointments, receiving immunizations, etc. In some embodiments, the subject's risk of exacerbation or recurrence of a dormant viral infection significantly increases under mental, physical, or environmental stress, as such stress impairs the body's ability to suppress the dormant infection or combat newly acquired infections.

In some embodiments, the volume of a single dose is 50 ul. In some embodiments, the volume of a single dose is from 25-50 ul. In some embodiments, the volume of a single dose is from 40-50 ul. In some embodiments, the volume of a single dose is from 50-60 ul. In some embodiments, the volume of a single dose is from 25-60 ul. The present invention is not limited to the aforementioned volumes of doses.

The prescribed dose (e.g., daily prescribed dose, weekly prescribed dose, etc.) dose of L-lysine may be administered by fractionated doses. In some embodiments, the fractionated doses, e.g., for achieving a daily prescribed dose, are separated by at least 10 minutes. In some embodiments, two fractionated doses are administered over the course of 1 hour. In some embodiments, two fractionated doses are administered over the course of 6 hours. In some embodiments, two fractionated doses are administered over the course of 12 hours. In some embodiments, two fractionated doses are administered over the course of 24 hours. In some embodiments, three fractionated doses are administered over the course of 12 hours. In some embodiments, three fractionated doses are administered over the course of 24 hours. In some embodiments, four fractionated doses are administered over the course of 12 hours. In some embodiments, four fractionated doses are administered over the course of 24 hours.

The methods of the present invention feature administering the pharmaceutical composition of the present invention. In certain embodiments, the methods comprise administering the pharmaceutical composition such that the subject receives a dose of 6 mg L-lysine in a day, e.g., the daily dose, e.g., a 24 hour period. In certain embodiments, the methods comprise administering the pharmaceutical composition such that the subject receives a dose of 6 mg L-lysine daily for two or more days, e.g., as needed.

In some embodiments, the daily dose of L-lysine is from 1 to 5 mg. In some embodiments, the daily dose of L-lysine is from 2 to 7 mg, e.g., 6 mg. In some embodiments, the daily dose of L-lysine is from 3 to 8 mg. In some embodiments, the daily dose of L-lysine is from 4 to 9 mg. In some embodiments, the daily dose of L-lysine is from 1 to 10 mg. In some embodiments, the daily dose of L-lysine is more than 10 mg.

In some embodiments, a single dose, e.g., a single administration, single drop, of L-lysine is from 0.1 to 2 mg, e.g., 1.5 mg. In some embodiments, a single dose, e.g., a single administration, single drop, of L-lysine is from 0.5 to 4 mg. In some embodiments, a single dose, e.g., a single administration, single drop, of L-lysine is from 1 to 2 mg. In some embodiments, a single dose, e.g., a single administration, single drop, of L-lysine is from 0.5 to 5 mg. In some embodiments, a single dose, e.g., a single administration, single drop, of L-lysine is from 1 to 6 mg. The present invention is not limited to the amounts of L-lysine in a single dose.

As a non-limiting example, the daily dose of ligustilide may be about 1.3 mg. In some embodiments, the daily dose of ligustilide is from 0.01 to 1 mg. In some embodiments, the daily dose of ligustilide is from 0.1 to 1 mg. In some embodiments, the daily dose of ligustilide is from 0.01 to 2 mg. In some embodiments, the daily dose of ligustilide is from 0.01 to 3 mg. In some embodiments, the daily dose of ligustilide is from 0.01 to 4 mg. In some embodiments, the daily dose of ligustilide is from 0.1 to 6 mg. In some embodiments, the daily dose of ligustilide is from 1 to 10 mg.

As a non-limiting example, the single dose (e.g., single administration, single drop) of ligustilide may be about 1.3 mg. In some embodiments, the single dose (e.g., single administration, single drop) of ligustilide is from 0.001 to 0.01 mg. In some embodiments, the single dose (e.g., single administration, single drop) of ligustilide is from 0.01 to 0.1 mg. In some embodiments, the single dose (e.g., single administration, single drop) of ligustilide is from 0.1 to 1 mg. In some embodiments, the single dose (e.g., single administration, single drop) of ligustilide is from 0.001 to 2 mg. In some embodiments, the single v of ligustilide is from 0.01 to 2 mg. In some embodiments, the single dose (e.g., single administration, single drop) of ligustilide is from 0.001 to 3 mg. In some embodiments, the single dose (e.g., single administration, single drop) of ligustilide is from 0.01 to 3 mg. In some embodiments, the single dose (e.g., single administration, single drop) of ligustilide is from 0.01 to 4 mg. The present invention is not limited to the amounts of ligustilide in a single dose.

The present invention is not limited to use in the treatment of FHV-1 in cats. The formulations herein may be used to treat other ocular conditions, such as but not limited to viral eye infections or inflammatory conditions, such as but not limited to keratoconjunctivitis sicca, dry eye disease (DED), follicular conjunctivitis, filamentary keratitis, graft vs. host disease, or the like.

EXAMPLES

The following are non-limiting examples of the present invention. It is to be understood that said example is not intended to limit the present invention in any way. Equivalents or substitutes are within the scope of the present invention.

Example 1—Preparation of Osha Root Extract (Ligustilide Solution) and L-Lysine Solution Osha Root Extract Preparation (e.g., Ligustilide Preparation)

Osha root is obtained, cleaned, and then dried before grinding into powder. The proper percentage weight to volume (e.g., 5%=5 g/100 mL) is added to a sterile solvent (e.g., water, or 20% EtOH or other as needed) and then heated to dissolve root and then allowed to cool prior to placing in 500 mL sterile 0.2 μm filter flask under negative pressure overnight. The fluid collected in the sterile chamber below is the osha root extract, e.g., ligustilide preparation. The osha root extract can then be added to the formulation, e.g., drop solution, in an appropriate concentration. The estimated concentration of the 5% osha root extract (e.g., ligustilide preparation) is 50 mg/ml, 5 mg/100 uL, or 2.5 mg/50 uL. A 10% osha root extract is 100 mg/ml, or 10 mg/100 uL, or 25 mg/50 uL.

If the concentration of ligustilide in the osha root extract is approximately 10%, then the concentration of ligustilide in a 5% (50 mg/ml) osha root extract preparation is 0.5%, or 5 mg/ml (or 0.5 mg/100 uL, or 0.25 mg/50 uL). If the concentration of ligustilide in the osha root extract is approximately 10%, then the concentration of ligustilide in a 10% (100 mg/ml) osha root extract preparation is 1%, or 10 mg/ml (or 1 mg/100 ul, or 0.5 mg/50 ul).

If the concentration of ligustilide in the osha root extract is approximately 20%, then the concentration of ligustilide in a 5% (50 mg/ml) osha root extract preparation is 1%, or 10 mg/ml (or 1 mg/100 uL, or 0.5 mg/50 uL). If the concentration of ligustilide in the osha root extract is approximately 20%, then the concentration of ligustilide in a 10% (100 mg/ml) osha root extract preparation is 2%, or 20 mg/ml (or 2 mg/100 uL, or 1 mg/50 uL).

If the concentration of the ligustilide in the osha root extract is approximately 5%, then the concentration of ligustilide in a 5% (50 mg/ml) osha root extract preparation is 0.25%, or 2.5 mg/ml (or 0.25 mg/100 uL, or 0.125 mg/50 uL). If the concentration of the ligustilide in the osha root extract is approximately 5%, then the concentration of ligustilide in a 10% (100 mg/ml) osha root extract preparation is 0.5%, or 5 mg/ml (or 0.5 mg/100 uL, or 0.25 mg/50 uL).

L-Lysine Preparation

Medical grade powdered L-lysine is obtained and weighed and added to a solvent (e.g., BSS, purified bacteriostatic H2O, or other appropriate solvents, e.g., as necessary for the solution) at the proper percentage weight to volume. The L-lysine-solvent mixture is mixed, e.g., stirred, at room temperature until completely dissolved and added to a sterile 0.2 μm filter flask and filtered and collected. The L-lysine preparation may be added to the pharmaceutical formulation of the present invention in an appropriate concentration.

A 3% L-lysine solution refers to 3 g/100 ml solvent, e.g., 30 mg/ml, 3 mg/100 uL, or 1.5 mg/50 uL.

A 5% L-lysine solution refers to 5 g/100 ml solvent, e.g., 50 mg/ml, 5 mg/100 uL, or 2.5 mg/50 uL.

Example 2—Treatment of FHV-1 in Cats

A study was performed with 2 cats in the same household with a known history of FHV-1.

Three preparations of the drops were produced. The preparations were as follows: (1) 3% (w/v) of L-lysine and 5% (w/v) of finely ground and brewed osha root, as described herein, combined with water and filtered through 0.20 um sterile syringes; (2) 3% L-lysine and 5% brewed osha root (as described herein) combined with sterile 50% solution BSS and sterile filtered; and (3) 3% L-lysine and 5% brewed osha root (as described herein) combined with 100% solution BSS sterile filtered. For reference: BSS refers to Balance Salt Solution for ocular irrigation. Each mL contains sodium chloride 0.64%, potassium chloride 0.075%, calcium chloride 0.048%, magnesium chloride 0.03%, sodium acetate 0.039%, sodium citrate 0.17%, sodium hydroxide/HCl to adjust pH to 7.5, osmolality is 300 mOsm/kg.

Each formulation was tested in both cats. For the first formulation, one drop was administered to both cats twice a day for four days. For the second formulation, one drop was administered to both cats twice a day for four days. For the third formulation, one drop was administered to both cats twice a day for four days.

Tolerability and reductions of symptoms were noted. Table 4 outlines the symptoms of each patient both prior to and following treatment. Table 4 also lists whether or not the treatment was effective (Y/N) based on the change in symptoms.

TABLE 4

| Cat | Symptoms prior to treatment | Symptoms after treatment | Was treatment effective? Y/N |
|---|---|---|---|
| 1 | Watery eyes, conjunctivitis | None | Y |
| 2 | Sneezing, watery eyes, conjunctivitis | None | Y |

It was surprisingly discovered that topical administration of a formulation comprising L-lysine in combination with z-ligustilide in a sterile ph-balanced topical eye drop formulation was effective for treating and reducing symptoms of FHV-1. Without wishing to limit the present invention to any theory or mechanism, it is believed that the formulations of the present invention have significant benefits over current treatment modalities in reducing the spread of FHV-1, relieving symptoms of FHV-1, treating FHV-1, and minimizing potentially blinding consequences resulting from FHV-1.

Example 3—Treatment of FHV-1 in Cats

A second study of two cats with a known history of FHV-1 utilizing 3% lysine in 0.9% NaCl and 5% Osha Root tea extract was shown to be well tolerated with relief of clinical signs according to the previously described MAGGS scoring System of FHV-1. Common observations of cats behavior after installation of drops were head shaking and rubbing eyes with paws.

| | |
|---|---|
| Conjunctival hyperemia | none |
| Chemosis | none |
| Conjunctival ulceration | none |
| Keratitis | none |
| Dendrite formation | n/a |
| Respiratory signs/Malaise | n/a |

Example 4—Treatment of FHV-1 Breakout in Cat Shelter

A study was performed with cats in a shelter following a breakout of FHV-1. Cats in the shelter were administered a pharmaceutical composition comprising 3% L-lysine in PH-balanced water. Technicians reported that there was a decrease in FHV-1 symptoms, and the formulation was well tolerated by the animals.

Example 5—Treatment of Viral Eye Infection in Dogs

Six dogs, each with a viral eye infection, present to a veterinarian. The veterinarian prescribes a pharmaceutical composition comprising 3% L-lysine and 5% ligustilide in sterile BSS. The dogs are administered one drop twice a day for 5 days, and their symptoms are recorded.

Example 6—Treatment of Viral Eye Infection in Humans

A patient presents to the emergency department with a viral eye infection. The physician prescribes a pharmaceutical composition comprising 3% L-lysine and 5% ligustilide in sterile BSS. The patient self-administers one drop twice a day for 5 days and records his symptoms.

The disclosures of the following U.S. Patents are incorporated in their entirety by reference herein: U.S. Pat. Nos. 8,623,852; 7,351,715; 6,455,061; 5,741,817.

As used herein, the term "about" refers to plus or minus 10% of the referenced number. For example, an embodiment wherein the formulation comprises 10% lysine includes a formulation comprising between 9% and 11% lysine.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A topical ophthalmic formulation comprising:
   a) a first therapeutic agent comprising ligustilide, wherein the concentration of ligustilide is about 5%; and
   b) a second therapeutic agent comprising L-lysine, wherein the concentration of L-lysine is about 1-5%.

2. The formulation of claim 1, wherein the formulation is an aqueous formulation.

3. The formulation of claim 2, wherein the aqueous formulation is in eye drop form.

4. The formulation of claim 1, wherein the ligustilide is extracted from Osha root.

5. The formulation of claim 1, wherein the concentration of L-lysine is about 3%.

6. The formulation of claim 1 further comprising a third therapeutic agent.

7. The formulation of claim 6, wherein the third therapeutic agent comprises one or a combination of an antihistamine, an anti-inflammatory agent, an immunosuppressive agent, a steroid, an antiviral agent, an antimycotic agent, or an anti-allergic agent.

8. The formulation of claim 1, wherein the formulation further comprises bacteriostatic water, bacteriostatic saline, polyethylene glycol, polyvinyl alcohol, propylene glycol, povidone, glycerine, mineral oil, a demulcent, or a combination thereof.

9. The formulation of claim 1 further comprising a buffer for ophthalmic applications.

10. The formulation of claim 1 further comprising a pharmaceutical carrier.

11. The formulation of claim 1, wherein the formulation is effective for preventing or treating feline herpesvirus-1 (FHV-1).

12. A topical ophthalmic formulation comprising ligustilide and L-lysine, wherein the concentration of L-lysine is about 1-5%.

* * * * *